United States Patent [19]

Wollenberg

[11] 4,450,281

[45] May 22, 1984

[54] PROCESS FOR THE PREPARATION OF A POLYALKENYL SUCCINIC ANHYDRIDE

[75] Inventor: Robert H. Wollenberg, San Rafael, Calif.

[73] Assignee: Chevron Research Company, San Francisco, Calif.

[21] Appl. No.: 454,398

[22] Filed: Dec. 29, 1982

[51] Int. Cl.³ .............................................. C07D 307/60
[52] U.S. Cl. ................................... 549/255; 560/190; 562/595
[58] Field of Search .................. 549/255; 560/190; 562/595

[56] References Cited

U.S. PATENT DOCUMENTS 3,952,023  4/1976  Kaiya et al. ..................... 549/255

Primary Examiner—Henry R. Jiles
Assistant Examiner—Bernard Dentz
Attorney, Agent, or Firm—D. A. Newell; J. M. Whitney; J. J. DeYoung

[57] ABSTRACT

Disclosed is a process for the preparation of substituted carboxylic acids and their derivatives in which the synthesis reaction is carried out at least partially thermally in the presence of a furan-type compound. The furan-type compound substantially increases yields and reduces the formation of undesirable resinous by-products.

8 Claims, No Drawings

PROCESS FOR THE PREPARATION OF A POLYALKENYL SUCCINIC ANHYDRIDE

FIELD OF THE INVENTION

This invention relates to an improved process for producing substituted carboxylic acids and their derivatives. More particularly, it relates to an improved process for the preparation of a polyalkenyl succinic anhydride for use as viscosity index improver.

BACKGROUND OF THE INVENTION

The preparation of substituted carboxylic acids and their anhydrides and esters from such unsaturated acids or acid derivatives as maleic anhydride, fumaric acid or itaconic acid has been known for some time. The products are useful in many ways. For example, they serve as anti-rust agents in lubricants and fuels and as intermediates in the preparation of metal salts, esters and nitrogen-containing products which are useful as viscosity index improvers, dispersants and the like in lubricants and fuels. Other uses are also known to those skilled in the art. For example, alkenyl succinic anhydrides are used in paper sizing, paper pulp processing, wet strength agents, epoxy curing agents, and plasticizer esters for polyvinyl chloride.

The methods heretofore used for the preparation of the substituted carboxylic acids comprise alkylation of the unsaturated acid or acid derivatives with an aliphatic hydrocarbon or halogenated aliphatic hydrocarbon at a temperature above about 200° C. The earliest commercial processes generally utilized a thermal reaction wherein polyolefins of average molecular weight above about 200 were thermally reacted with maleic anhydride at temperatures in excess of 200° C. However, this thermal reaction suffers from a relatively low degree of conversion and if an attempt is made to improve the degree of conversion by increasing the temperature of pressure, an undesirable degradation of maleic anhydride occurs with resulting formation of carbon dioxide, water and tarry solids (resin). For this reason, resort has been made to initial preparation of a halogenated hydrocarbon reactant followed by reaction of the halogenated hydrocarbon with maleic anhydride (chlorination processes).

However, in these chorination processes, a relatively high concentration of chlorine is in contact with the reaction vessel for substantial lengths of time, necessitating the use of special equipment for the entire reaction and the final product frequently contains undesirable residual chlorine. In attempts to overcome the problems associated with both the thermal and chlorination processes, researchers have devised various multistage processes and processes utilizing combinations of the thermal process and chlorination process. See for example, U.S. Pat. Nos. 3,231,587; 3,912,764; and 4,110,349.

The present invention is also related to the invention in my copending application Ser. No. 373,471, filed Apr. 4, 1982, entitled "Process for Preparation of Alkenyl Succinic Anhydrides" now U.S. Pat. No. 4,388,471, in which the alkylating hydrocarbon contained one olefin bond in contrast to the present invention in which the alkylating hydrocarbon contains two or more olefinic bonds.

SUMMARY OF THE INVENTION

It has been found that in a process for preparing a substituted carboxylic acid or derivative thereof from the thermal reaction of (A) a hydrocarbon containing two or more olefinic double bonds with (B) at least one of maleic acid, fumaric acid, itaconic acid and anhydrides and esters of these acids, that carrying out the reaction in the presence of a furan-type compound increases yields and reduces the formation of undesirable resinous by-products.

DETAILED DESCRIPTION OF THE INVENTION

As noted hereinabove, the chemicals used in the method of this invention are (A) a suitable alkylating hydrocarbon; (B) maleic, fumaric or itaconic acid or an anhydride or ester thereof; and a furan-type compound. If Reagent (B) is an ester, it is preferably a lower alkyl ester, the word "lower" denoting radicals having up to 7 carbon atoms. Most often, Reagent (B) is the free acid or the anhydride, and it is preferably maleic anhydride.

The alkylating hydrocarbon constituting Reagent (A) is a hydrocarbon which contains two or more olefinic double bonds but is otherwise substantially saturated or contains an aromatic ring. The olefinic double bonds may be conjugated or nonconjugated. Suitable hydrocarbons include diolefins, olefinic petroleum fractions and polyunsaturated polymers, oligomers, and copolymers. The invention will be described hereinafter principally with reference to polyunsaturated polymers made from olefins and diolefins. These latter are the preferred feed components (A).

The polyunsaturated polymers are usually those prepared by copolymerization of lower monoolefins with lower diolefins. Both types of olefins contain up to 12 carbon atoms. Suitable monoolefins include ethylene, propylene, 1-butene, 2-butene, isobutene and the pentenes, hexenes and heptenes (all isomers included). Suitable diolefins include butadiene, 1,5-hexadiene, norbornadiene 1,5-dodecadiene, and the like.

Furthermore, the olefin polymer can contain alicyclic or aromatic carbon atoms which may be derived from such monomers as cyclopentene, cyclohexene, 1,4-cyclohexadiene methylene cyclopentene, methylene cyclohexene, α-pinene, styrene, vinyl toluene, α-methylstyrene, and 3-phenyl-1,5-hexadiene.

The preferred olefin polymers are those derived from monoolefins copolymerized with diolefins, especially mono-1-olefins and more especially two to six carbon mono-1-olefins such as ethylene, propylene and the butenes copolymerized with diolefins. The copolymers (also called interolymers) may be ordinary chain copolymers or graft copolymers as long as they contain more than one olefinic double bond. The preferred copolymer is derived from butadiene and styrene.

Furthermore, terpolymers and higher polymers can also be employed in this invention. Any of the above listed olefins and diolefins can be used to prepare these multicomponent polymers. The perferred terpolymer is made fro ethylene, propylene and butadiene.

The olefin polymer usually contains about 30–75,000 and preferably about 50–50,000 carbon atoms. The number average molecular weight of the polymer, as determined by gel permeation chromatography, is ordinarily about 400–1,000,000, especially about 700–100,000.

In addition to the above-described alkylating hydrocarbons, many other alkylating hydrocarbons can be used. Other suitable alkylating hydrocarbons include alpha or internal diolefins having cyclic, linear, or branched structure with molecular weights in the range 54–1,000,000 or more with molecular weights in the range of 200–100,000 being more preferred. Internal diolefins are easily obtained by the isomerization of alpha-omega diolefins over a suitable catalyst such as silica.

As will be apparent from the above description, mixtures of alkylating hydrocarbons can be used as Reagent (A). It is also within the scope of the invention to use mixtures of polymers of different monomer combinations, such as ethylene/propylene/1,5 hexadiene terpolymer with a styrene/butadiene copolymer, or the like.

Mixtures of acids, anhydrides and/or esters may be used as Reagent (B); illustrative are maleic acid-fumaric acid mixtures, mixtures of methyl itaconate and methyl maleate, and mixtures of maleic acid and maleic anhydride. Most often, however, it is convenient and therefore desirable to use a single reagent as Reagent (B).

As used in the present invention, "furan-type compound" means a five-membered, oxygen-containing, heterocyclic-ring compound having two double bonds in the ring. Representative compounds include: furan, alkyl or dialkylfurans such as 3,4-dimethylfuran, 2,5-dimethylfuran, 2,3-dimethylfuran, 3-methylfuran, 3,4-diethylfuran, 3-t-butylfuran, etc. The alkyl group may contain 5 or more carbon atoms but preferably the alkyl group will contain 1–4 carbon atoms. Other furan-type compounds include furfural, furanoic acid, and benzofuran.

The molar ratio of Reagent (A) to Reagent (B) may vary according to the proportion of acid or acid derivative radicals desired in the product. Typically, about 0.2–2.0 moles of Reagent (B) are used per mole of Reagent (A), but it is usually desirable to use 0.5–1.5 moles and more preferably at least 1 mole of Reagent (B) per mole of Reagent (A) so as to minimize the amount of unreacted olefin polymer present in the product.

The reaction of Reagents (A) and (B) is carried out in the presence of an effective amount of the furan-type compound. By "an effective amount" is meant an amount sufficient to substantially reduce the formation of resinous by-products. Generally, these resinous by-products are believed to be formed by the homopolymerization of the acid or acid derivatives [Reagent (B)]. Generally, this amount will range from 0.05–4.0 or more moles of furan-type compound per mole of Reagent (B), preferably 0.1–1 moles and more preferably 0.4–0.6 moles per mole of Reagent (B). It is believed that very small quantities of the furan-type compound may be effective in preventing resin formation. Although the formation of these resinous by-products is not completely understood, and with the understanding that Applicant does not wish to be bound by any particular theory, it is believed that the furan-type compound may undergo a reversible, cyclo addition, Diels-Alder-type reaction with the olefinic-bonded carbon atoms of the maleic anhydride thereby forming a thermally unstable compound which serves to substantially reduce the quantity of "free" maleic anhydride available for reaction at any particular time. Maintaining the quantity of "free" maleic as low as possible in the reaction mixture is believed to prevent the polymer formation.

The reaction can be carried out continuously or in a batch process and may be carried out in one or more stages, as is well known in the art. Furthermore, the process of this invention can be utilized in combination processes, e.g., the first step can be carried out as described herein and after separation of the furan-type compound, the second step may be carried out in the presence of chlorine. Preferably, the entire reaction is carried out thermally in the presence of the furan-type compound. The temperature employed may be in the range 50°–300° C., preferably 180°–285° C., and most preferably 200°–270° C. After the reaction, the furan-type compound can be stripped or separated from the reaction mixture by methods well known in the art.

The process will be further illustrated by the following representative examples.

EXAMPLES

Example 1

Polyalkenyl Succinic Anhydride Synthesis with Furan

Polyalkenyl succinc anhydirde (PASA) was prepared as follows: Approximately 210 grams of an ethylene/propylene/butadiene terpolymer having a molecular weight of about 100,000 was diced into ¼ inch cubes and added slowly to 820 grams of light hydrocarbon (Cities 350 neutral). The cubes were added over one hour to the 175° C. preheated hydrocarbon. The oil was cooled and charged with 16.0 mL of maleic anhydride and 6.3 mL of furan. The mixture was sparged with nitrogen and reheated to 150° C. for 2 hours. The temperature was then raised to 245°–255° C. and held for 18 hours. After cooling and thorough mixing of the reaction product, a 25-mL sample was removed for sediment (resin) analysis. The sample was diluted with 75 mL of hexane and centrifuged at 6000 rpm for 15 minutes. The sample contained 0.09 weight percent sediment (resin). Infrared analysis indicated that one mole of maleic anhydride had reacted per 3300 mole weight of polymer. The infrared absorption curve showed a strong broad peak centered at 1877 cm$^{-1}$ and a smaller peak at 1803 cm$^{-1}$.

Example 2

Polyalkenyl Succinic Anhydride Synthesis Without Furan

The same procedure and amounts described in Example 1 was followed except furan was omitted. The reaction was conducted initially at 150° C. and then at 245°–255° C. Analysis of a small sample indicated 4.6 weight percent sediment (resin) and infrared indicated that one mole of maleic anhydride had reacted per 5500 mole weight of polymer. The infrared absorption curve was identical with that of the previous example.

Comparison of Examples 2 with 1 demonstrates the large reduction in the quantity of resinous waste products from 4.6 weight percent to 0.09 weight percent, and the higher degree of conversion when carrying out the reaction in the presence of a furan-type compound.

It will be understood that various modifications of the invention can be practiced by those skilled in the art without departing from the scope and spirit of the invention.

What is claimed is:

1. In a method for preparing a substituted carboxylic acid or derivative thereof which comprises reacting (A) an alkylating hydrocarbon containing two or more double bonds with (B) at least one of maleic acid, fumaric acid, itaconic acid and anhydrides and esters of any of these acids, at least part of the reaction being conducted thermally, the improvement which comprises conducting said thermal reaction in the presence of a furan-type compound.

2. The method according to claim 1 wherein said thermal reaction is carried out in the presence of an effective amount of said furan-type compound to substantially reduce the formation of resinous by-products.

3. A method according to claim 2 wherein Reagent (A) is a diolefin polymer.

4. A method according to claim 3 wherein Reagent (B) is maleic anhydride.

5. A method according to claim 4 wherein said furan-type compound is selected from furan, 3,4-dimethylfuran, 2,5-dimethylfuran, or furfural.

6. A method according to claim 5 wherein said reaction is conducted in the presence of 0.05–4.0 moles of said furan-type compound per mole of Reagent (B).

7. A method according to claim 2 wherein Reagent (A) is an ethylene/propylene/butadiene terpolymer, Reagent (B) is maleic anhydride, and said furan-type compound is furan which is present in said reaction in the range of 0.1–1.0 moles per mole of maleic anhydride.

8. A method of claim 7 wherein said reaction is carried out thermally at a temperature in the range 180°–275° C.

* * * * *